US008888706B2

(12) United States Patent
Chen et al.

(10) Patent No.: US 8,888,706 B2
(45) Date of Patent: Nov. 18, 2014

(54) DUAL-CURVATURE PHASED ARRAY HIGH-INTENSITY FOCUSED ULTRASOUND TRANSDUCER FOR TUMOR THERAPY

(75) Inventors: Gin-Shin Chen, Miaoli County (TW); Hsu Chang, Fremont, CA (US); Win-Li Lin, Taipei (TW)

(73) Assignee: National Health Research Institutes, Zhunan Town (TW)

( * ) Notice: Subject to any disclaimer, the term of this patent is extended or adjusted under 35 U.S.C. 154(b) by 860 days.

(21) Appl. No.: 12/535,235

(22) Filed: Aug. 4, 2009

(65) Prior Publication Data
US 2011/0034808 A1 Feb. 10, 2011

(51) Int. Cl.
| | | |
|---|---|---|
| A61B 8/14 | (2006.01) | |
| A61N 7/02 | (2006.01) | |
| B06B 1/06 | (2006.01) | |
| G10K 15/04 | (2006.01) | |
| A61N 7/00 | (2006.01) | |
| A61B 8/12 | (2006.01) | |

(52) U.S. Cl.
CPC ................ *A61N 7/02* (2013.01); *B06B 1/0637* (2013.01); *A61N 2007/0095* (2013.01); *A61B 8/12* (2013.01); *A61N 2007/0078* (2013.01); *G10K 15/043* (2013.01)
USPC ................................ 600/459; 606/32; 73/642

(58) Field of Classification Search
USPC ......... 600/395, 407, 437, 443, 447, 459, 463; 438/109, 110, 118, 124, 125; 310/311, 310/313, 322, 323; 356/4.01, 4.07, 5.04, 356/479, 489, 495, 497, 515
See application file for complete search history.

(56) References Cited

U.S. PATENT DOCUMENTS

| | | | | |
|---|---|---|---|---|
| 4,557,146 A | * | 12/1985 | Buffington et al. | ............. 73/642 |
| 5,176,140 A | * | 1/1993 | Kami et al. | ................... 600/459 |
| 6,540,677 B1 | * | 4/2003 | Angelsen et al. | ............ 600/437 |
| 6,613,004 B1 | * | 9/2003 | Vitek et al. | ......................... 601/2 |
| 7,307,374 B2 | * | 12/2007 | Ossmann | ...................... 310/335 |
| 2003/0055308 A1 | * | 3/2003 | Friemel et al. | ................... 600/15 |
| 2005/0240127 A1 | * | 10/2005 | Seip et al. | .......................... 601/2 |
| 2005/0272183 A1 | * | 12/2005 | Lukacs et al. | ................. 438/109 |
| 2006/0094988 A1 | * | 5/2006 | Tosaya et al. | ...................... 601/2 |
| 2007/0035201 A1 | * | 2/2007 | Desilets et al. | ............... 310/311 |
| 2007/0167705 A1 | * | 7/2007 | Chiang et al. | ................. 600/407 |

OTHER PUBLICATIONS

Lin, Che-Yu, "Curved Cylindrical Ultrasound Phased Array for Liver Tumor Therapy," Institute of Biomedical Engineering, College of Engineering and College of Medicine, National Taiwan University, Jul. 2008 (117 pages) English Abstract.

* cited by examiner

*Primary Examiner* — Unsu Jung
*Assistant Examiner* — Michael N Fisher
(74) *Attorney, Agent, or Firm* — Occhiuti & Rohlicek LLP (57) ABSTRACT

A transducer for use with a high intensity focused ultrasound medical system has transducer elements that are made from a piezocomposite material bonded together in turn with an adhesive. The elements are deployed along a surface of a geometric structure with two curvatures. The structure is a truncated curved cylinder. The transducer also includes electrodes, each of which is arranged on a corresponding one of the transducer elements for exciting the transducer elements to emit ultrasonic waves in response to electrical signals applied to the electrodes to steer the waves to form a common focus zone in a desired heating area.

13 Claims, 14 Drawing Sheets

DUAL-CURVATURE PHASED ARRAY HIGH-INTENSITY FOCUSED ULTRASOUND TRANSDUCER FOR TUMOR THERAPY

FIELD OF DISCLOSURE

This disclosure relates to ultrasound, and in particular, to high-intensity focused ultrasound.

BACKGROUND

Transducers designed for therapeutic ultrasound applications deliver therapeutic power levels through piezoelectric ceramics such as PZT (Lead Zirconate Titanate) or through PZT/polymer composites. The transducer consists of a single piezoelectric element or multiple elements. Electrodes are connected to each piezoelectric element to generate ultrasound waves and to control wave properties such as frequency, amplitude and phase of ultrasound waves. The single element transducer has a fixed focal length that generates a fixed focal position, while the phased array (with multiple elements) transducer possesses the ability to steer the focus position by tuning each element's phase, which is called beam forming.

Therapeutic ultrasound is a minimally invasive or non-invasive method for depositing acoustic energy into tissue. The most common therapeutic application for an ultrasound transducer is to deliver focused ultrasound or High Intensity Focused Ultrasound (HIFU) to heat and destroy pathogenic tissue or to help drug delivery and release inside the body. Therefore, a therapeutic ultrasound transducer is designed to deliver acoustic energy through multiple layers of human skin, fat, muscle and soft tissues and to focus an acoustic beam at one specific zone under such layers. The precision with which the focus position is steered the energy level at the focus position are critical. Moreover, dynamic focusing of the transducer is required to track and target tumors in the moving organ, e.g. liver tumors.

SUMMARY

It is an object of this invention to provide a transducer having a wide focus-steering range in two dimensions.

It is a further object to use a dual-curvature phased array transducer in a HIFU (high-intensity focused ultrasound) medical system and to provide a method to determine the ratio of radii of two curvatures.

These and other objects of the invention will be understood by those skilled in the art with reference to the following summary, detailed description, and the attached drawings.

A transducer for use with a high intensity focused ultrasound medical system comprises a plurality of transducer elements that are made from piezocomposite material. These transducer elements are bonded together in turn with an adhesive and transducer elements deployed along a surface of a curved cylindrical geometric structure with two curvatures. A plurality of electrodes are arranged on the transducer for exciting the transducer elements in different phases to emit ultrasonic waves in response to electrical signals applied to the electrodes to steer the ultrasonic waves so as to form a common focus center in a desired heating area.

Other and further aspects and features of the invention will be evident from reading the following detailed description of the drawings, which is intended to illustrate, not limit, the invention.

BRIEF DESCRIPTION OF THE DRAWINGS

Various embodiments of the present invention are described and illustrated herein with reference to the drawings in which like items are indicated by the same reference, in which:

FIG. 4 (a) is a diagram of a spherical transducer.

FIG. 4 (b) is a diagram of a cylindrical transducer.

FIG. 6 (a) is a diagram of a spherical transducer in a three-dimensional coordinate system.

FIG. 6 (b) is a diagram of a dual-curvature transducer in a three-dimensional coordinate system.

FIG. 7 (a) shows intensity as a function of ratio of radii of curvature.

FIG. 7 (b) shows half beam width as a function of radii of curvature.

FIG. 8 (a) is a diagram to show a cross-sectional view of a simulated acoustic field in the XZ-plane.

FIG. 8 (b) is a diagram to show a cross-sectional view of a simulated acoustic field in the YZ-plane.

FIG. 9 (a) is a diagram to show the steering ability in the depth/Z direction.

FIG. 9 (b) is a diagram to show the steering ability in the depth/Z direction.

FIG. 9 (c) is a diagram to show the steering ability in the depth/Z direction.

FIG. 10 (a) is a diagram to show the steering ability in the X direction.

FIG. 10 (b) is a diagram to show the steering ability in the X direction.

FIG. 10 (c) is a diagram to show the steering ability in the X direction.

DETAILED DESCRIPTION OF THE PREFERRED EMBODIMENTS

When a single element HIFU transducer is employed to deliver energy over a target region, typically a mechanical motion control is used to move the focal zone of the transducer. More advanced designs of HIFU transducers use a phased array transducer. Each transducer element in the phased array is a small and independent transducer. Each transducer element is bonded together in turn with epoxy or other adhesives on a surface. Those transducers are connected to electrodes so that the relative phases of elements in the array can be electrically adjusted. Each element in the array is dynamically adjusted to deliver an acoustic wave with a different phase. Different phases from different elements create constructive interference of the wave fronts. As a result, delivered energy can be focused at different depths and angles and the position of the focal zone can be controlled.

Figure 1:
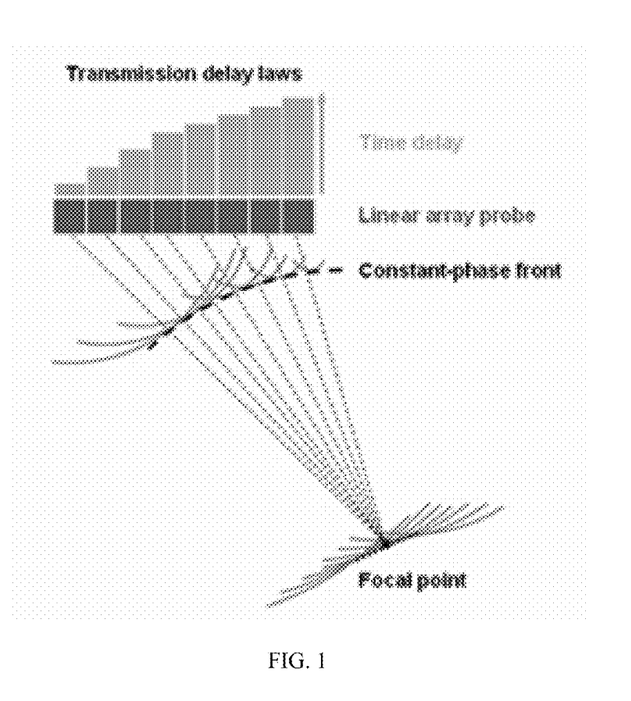
FIG. 1 is a diagram to visualize the principle of focus phased array.

The principle of a phased array is shown in FIG. 1. FIG. 1 shows that by using different phases on each element, an ultrasonic beam is steered to a focal point.

Figure 2:
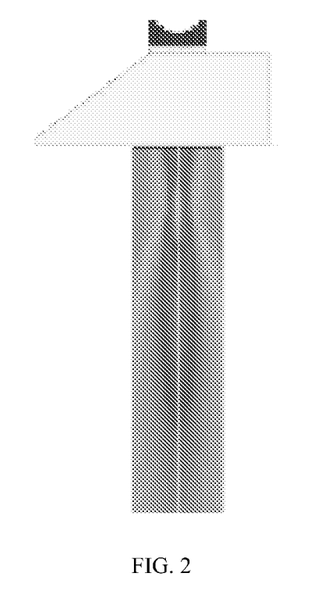
FIG. 2 is a diagram showing a sharp focal zone generated by a flat transducer.
Figure 3:
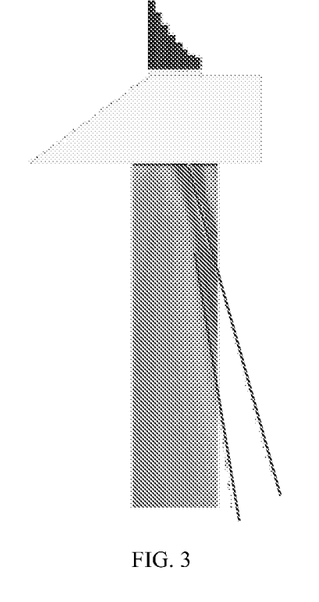
FIG. 3 is a diagram showing a focal zone generated and steered by a flat transducer.
Figure 4:
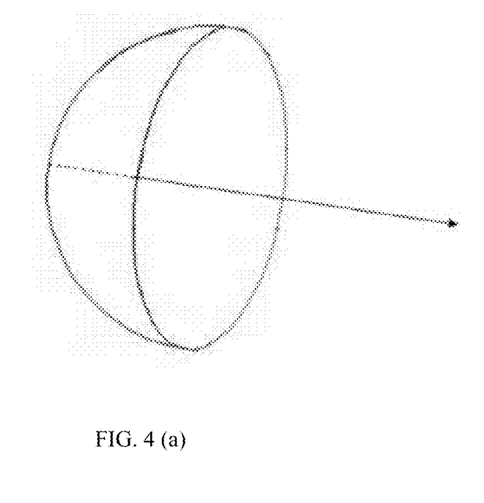

Other possible control results are shown in FIG. 2. FIG. 2 shows a sharp focal zone generated by a flat transducer having a phased array configuration. A conventional spherical transducer can obtain the desired focal point and achieve same result. However, such a conventional transducer cannot be steered to focus at a specific angle, as shown in FIG. 3. Therefore as piezocomposite technology has developed, a spherical transducer or a cylindrical transducer with a phased array configuration has been constructed. As shown in FIG. 4 (a) and FIG. 4 (b), a phased array transducer with a spherical section can steer the focus along a center line; and a phased array transducer with a cylindrical section has a focus-steering ability along the cylindrical long axis. An advantage of using electrical phase adjustment is that it increases the ability to control movement of focal location, which is one of the critical factors of HIFU system. Dr. Hynynen has used a 1.1 MHz, 256-element spherical phased array HIFU transducer with a 10 cm radius of curvature and a 12 cm diameter to generate multiple foci simultaneously in a 7.5 mm by 7.5 mm region and to provide a dynamic focusing in the depth direction.

In accordance of present invention, a dual-curvature (DC) phased array HIFU transducer is proposed and its feasibility proven via the numerical simulations.

Figure 5:
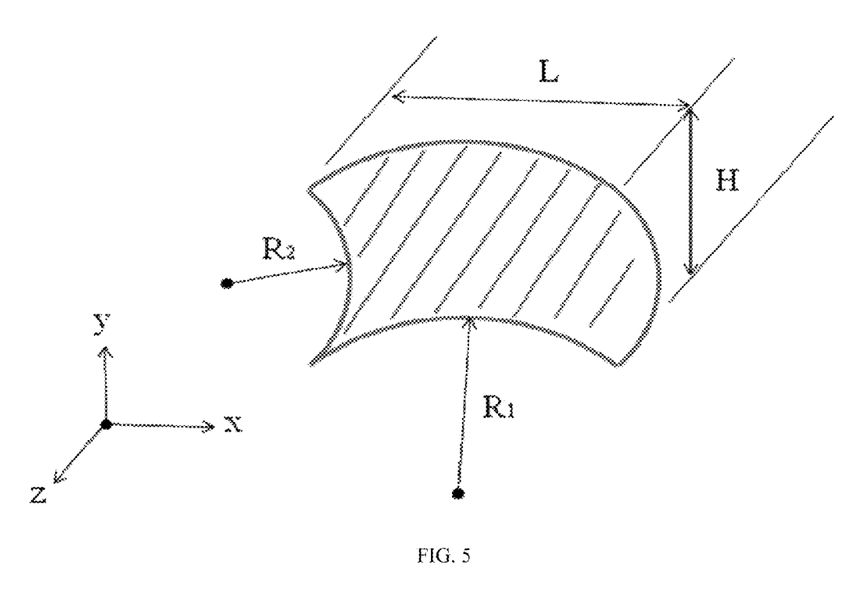
FIG. 5 is a diagram of a dual-curvature phased array HIFU transducer.

As shown in FIG. 5, the geometric shape of the DC phased array HIFU transducer (hereinafter referred to as "DC transducer") is curved cylindrical. The DC transducer consists of several hundred elements, each of which is made of piezoelectrical/piezocomposite material. With two radii of curvature, R.sub.1 and R.sub.2, the DC transducer has two natural focal zones, and acoustic beams can converge on two zones when the input electrical phase of all elements is the same. After some fine adjustment of the phases of all the elements, the two foci merge into one focal zone, which can then be steered in the Z or X directions via further adjustment of the phases. With an appropriate arrangement of the DC transducer on a patient's torso, the merged focal zone is able to follow a target that moves as a result of respiration, thus allowing the transducer to perform local thermal therapy and/or drug delivery. For instance, the X direction aligns to the head-to-toe direction and the Z direction denotes the depth direction.

Figure 6:
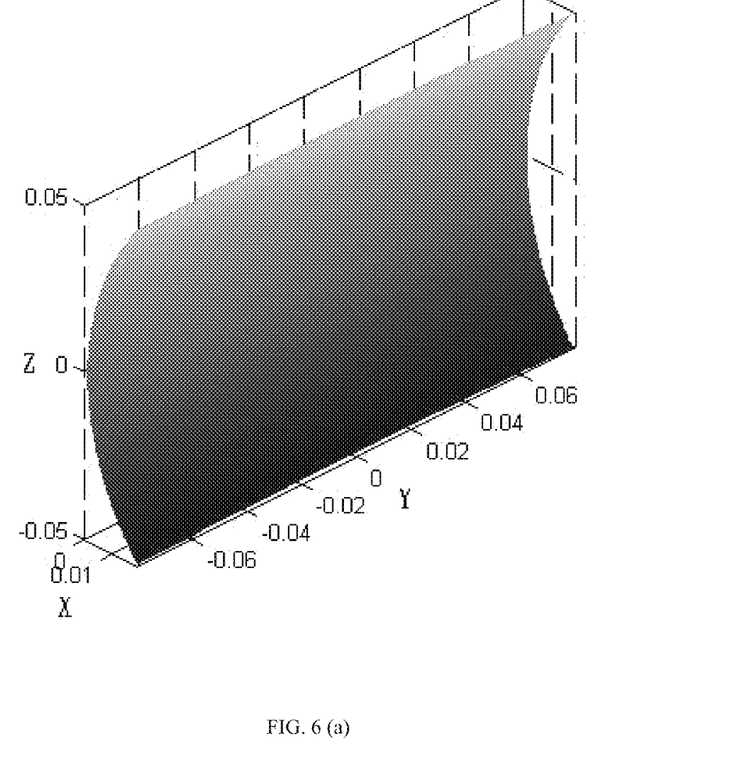

An embodiment of the present invention is shown in FIG. 6 (a) and FIG. 6 (b).

FIG. 6 (a) shows a cylindrical phased array HIFU transducer with its long axis in the X direction. The array's radius of curvature for every cross section in the YZ plane is fixed. For a cut along the XZ plane, the intersection is a line; therefore the radius of curvature is infinite.

The DC phased array HIFU transducer as shown in FIG. 6 (b) obtains different results. Its radius of curvature for every cross section in both the XZ plane and the XY plane is not fixed. Therefore the curvature in XY plane also contributes to the array's focusing ability. The geometry structure of the DC phased array includes at least two cylindrical curvatures and combines features of both cylindrical and spherical phased array HIFU transducers.

More detailed design information to implement the foregoing embodiments follows.

First, the number of elements is determined by consideration of the ability to focus steering and by the cost of an amplifier. Theoretically, the more elements there are, the better the array becomes at steering its focus. Nonetheless, more elements increase the complexity and cost of the phase and power generator. In the case of the liver tumor therapy, a minimum number of elements is required to make the steering range of the DC transducer sufficient for tracking a moving tumor.

Second, in view of the direction of movement and displacement of the liver tumor during a patient's respiration, more elements are arranged in the X direction of the DC transducer to provide a wide range for steering the focus in the head-to-toe direction. Additionally, to reduce the number of channels and the overall cost of the power amplifier, one can utilize symmetry to simplify control of the elements. In one example, the elements in the Y direction are connected in pairs and symmetrically with respect to the center line of the DC transducer along the X-axis.

Third, in order to avoid skin burn during the HIFU sonications, the DC transducer preferably has a wide aperture. Moreover, the surface acoustic intensity, defined as the acoustic power of total elements divided by the aperture area, restricts the aperture area. This surface acoustic intensity depends on material properties of the piezoelectrical/piezocomposite material.

Fourth, the length, L, height, H, and the radii of two curvatures, R.sub.1, R.sub.2 of the DC transducer as shown in FIG. 5 are related to the focus-steering range in the depth direction, the diameter and length of an ellipsoidal focus, and the spatial averaged intensity at the focus. With the design of two curvatures, the depth-directional focusing of the DC transducer can steer enough to treat the whole liver. The f#1 is the f number 1 defined as R.sub.1 divided by L, and f#2 is the f number 2 defined as R.sub.2 divided by H. The diameter of the focus is linearly proportional to the f#1 and the length of the focus is linearly related to the square of f#2. The ratio of R.sub.2 to R.sub.1 is optimized by taking into account the focus-steering range in the depth direction and the spatial averaged intensity at the focus.

TABLE 1 shows one example of dimensions of a DC phased array HIFU transducer

TABLE 1

| | |
|---|---|
| L (mm) | 160 |
| H (mm) | 100 |
| $R_1$ (mm) | 240 |
| $R_2$ (mm) | 160 |
| The number of element | 512 |
| Size of one element (mm) | 2.55 by 12.75 |

It should be noted that in one embodiment, among a total 512 elements there are 64 independently-driven elements in the X direction and 8 symmetrically driven elements in the Y direction.

To be effective, the absorbed acoustic power at the desired focal point should be greater than a certain amount. A numerical simulation of energy delivering and absorption is beneficial to the design of the transducer according to this invention. Here by using the Rayleigh-Sommerfeld principle to integrate the contribution of each point source on the surface of the transducer, the absorbed acoustic power deposition q is given as $$q = \frac{\alpha |p|^2}{\rho c}$$

where $\alpha$ is the ultrasound absorption coefficient of tissue, p is the ultrasonic pressure, $\rho$ is the tissue density, and c is the speed of sound in tissue. Values for $\alpha$, $\rho$, and c used in the simulation were 8.86 Np/m at 1 MHz, 1000 kg/m.sup.3, and 1500 m/s. The driving signals for the transducer elements that produce a specific focused pattern are calculated by a pseudo inverse method, and the driving frequency is 1 MHz.

Figure 7:
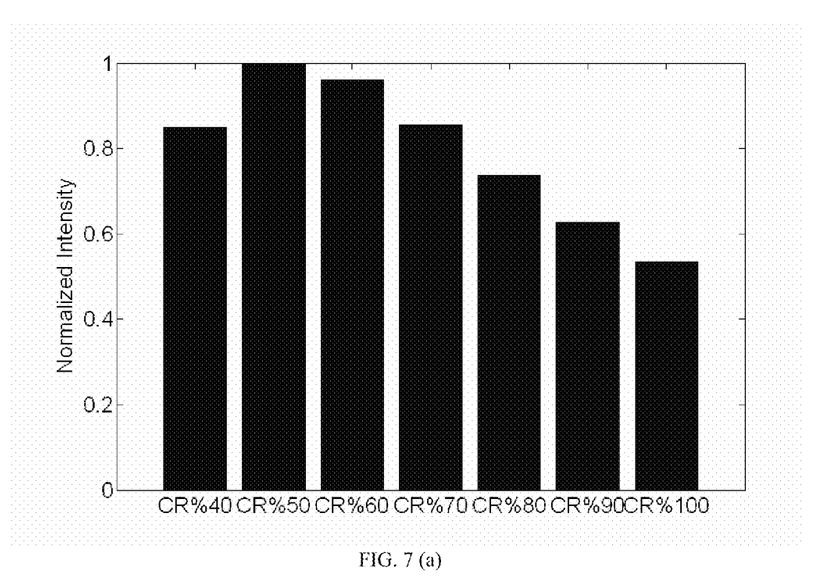

The results of simulation, as shown in FIG. 7 (a), demonstrate that the intensity is strongest when the CR is 50%, where CR is defined as the ratio of R.sub.2 to R.sub.1, but the half beam width in the depth direction, which is defined as the depth-directional focus-steering range, is only 4 cm, as shown in FIG. 7(b). This is not sufficient for liver treatment. With the trade-off between the intensity and half beam width in the depth direction, the optimal CR for use in liver therapy is in the range of 60% to 70%.

Figure 8:
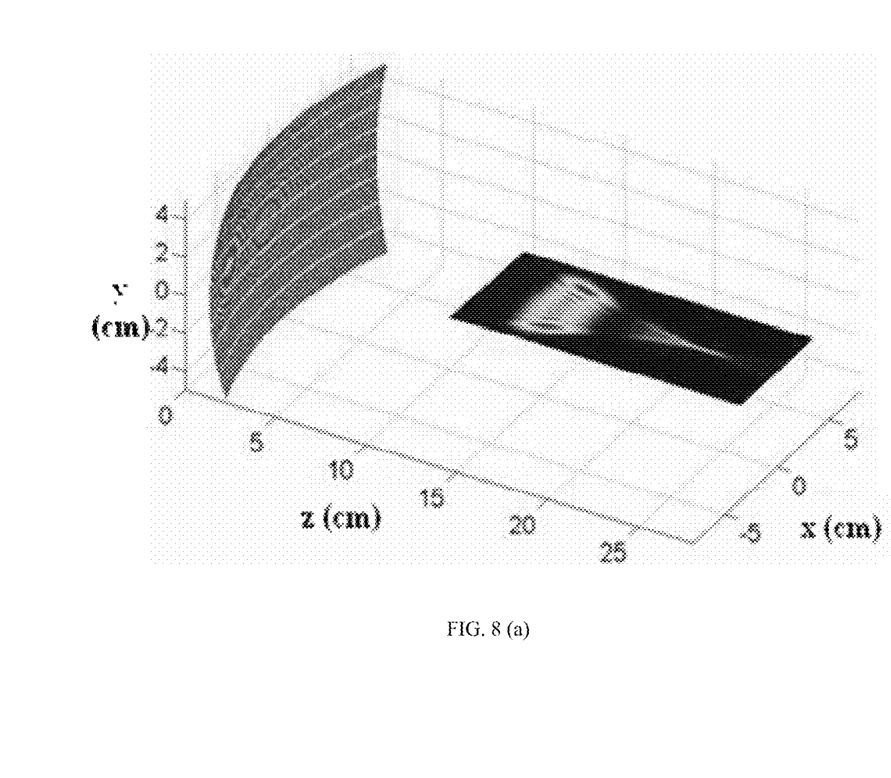
Figure 9:
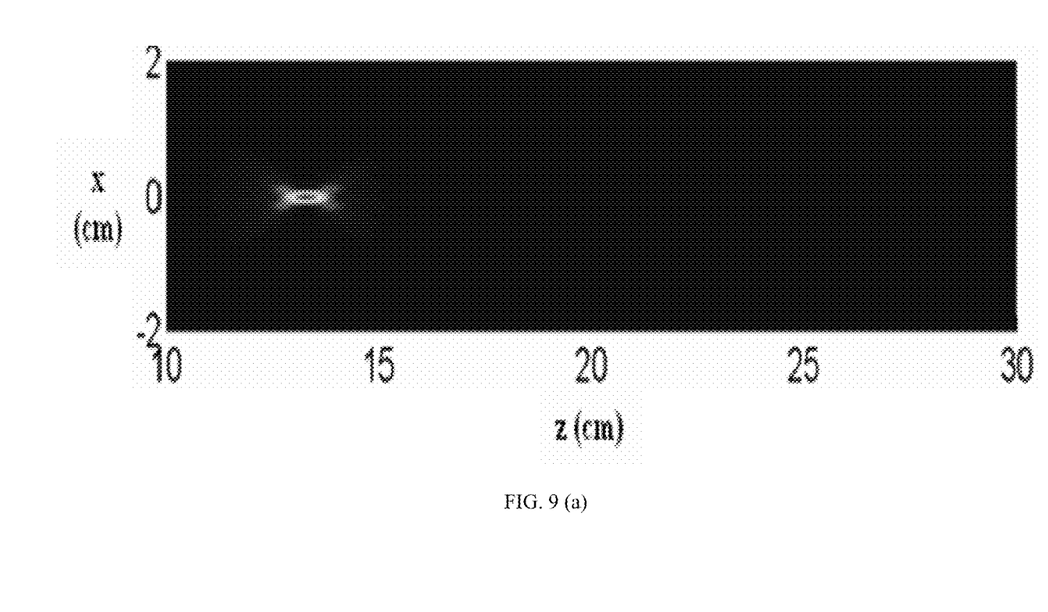

FIG. 8(a) and FIG. 8(b) illustrate the focusing status of the DC transducer when the electrical phases of the elements are all the same. All acoustic beams generated by the elements converge on the limited region at two geometric foci. One is at a location 16 cm away from the center of the DC transducer as shown in FIG. 8(a). The focal zone, defined as the area with a peak intensity within −6 dB peak intensity, is on the center XZ plane distributed along the X axis. The distance between the other focal zone and the center of the DC transducer is 24 cm. This focal zone is on the center YZ plane distributed along the Y axis and perpendicular to the X axis as shown in FIG. 8(b). After the tuning of each element's phase, two focal zones can merge into one focal zone and the focal zone can be steered in the depth/Z direction as shown in FIG. 9(a), FIG. 9(b) and FIG. 9(c). When the focal zone stays at the points (0, 0, 13 cm), (0, 0, 15.5 cm), and (0, 0, 19 cm) where the center of the DC transducer is the original point (0, 0, 0), the maximum intensity at the three locations is 6639, 10275, and 5843 W/cm.sup.2, respectively. These intensities are strong enough to cause necrosis of the liver tumor or to release the targeted drug. Therefore, the depth-directional focus-steering range of the DC transducer is from 13 cm to 19 cm measured from the center of the transducer.

Figure 10:
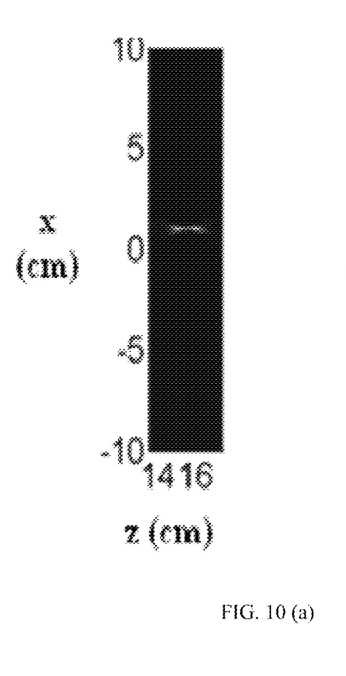

Moreover, the results of evaluating the X-axial focus-steering ability of the DC transducer are shown in FIG. 10(a), FIG. 10(b) and FIG. 10(c). It can be observed that the focusing performance remains good while steering from the point (1 cm, 0, 15.5 cm) in FIG. 10(a) to the point (3 cm, 0, 15.5 cm) in FIG. 10(c). The intensities at three points in this range are 12453, 10280, and 7420 W/cm.sup.2, respectively. These intensities are high enough to ablate tumor tissue or to activate an anti-tumor drug. Therefore, the DC transducer can steer the focal zone in the X direction from −3 cm to 3 cm measured from the center of the transducer.

The invention claimed is:

1. An apparatus comprising a dual-curvature transducer array for use with a high intensity focused ultrasound medical system, said dual-curvature transducer array comprising: a plurality of transducer elements that are made from piezocomposite material; said plurality of transducer elements bonded together with an adhesive and deployed along a surface of a geometric structure with two curvatures, said geometric structure comprising a truncated torus and a plurality of electrodes, each of which is arranged on a corresponding one of said transducer elements for exciting said transducer elements to emit ultrasonic waves in response to electrical signals applied to said electrodes to steer said waves to form a common focus zone in a desired heating area.

2. The apparatus of claim 1, wherein said adhesive comprises an epoxy.

3. The apparatus of claim 1, wherein said electrical signal controls a frequency, phase, and amplitude of said ultrasonic waves, thereby driving said transducer to focus said ultrasonic waves at a high-intensity focal zone.

4. The apparatus of claim 1, wherein said geometric structure has a first radius of curvature and a second radius of curvature, and wherein a ratio of said second radius of curvature to said first radius of curvature is predetermined to optimize an intensity of acoustic energy absorption and a focus-steering range in said desired heating area.

5. The apparatus of claim 1, wherein said transducer contains no ferromagnetic material so that said transducer can work within a magnetic resonance imaging system.

6. The apparatus of claim 1, wherein said surface of a geometric structure with two curvatures is disposed in a coordinate system having a first coordinate axis extending from said surface toward said common focus zone, a second coordinate axis transverse to said first coordinate axis, and a third coordinate axis transverse to said first and second coordinate axes, and wherein said electrical signals are selected to form a focal zone, movement of said focal zone in response to changes in phases of said electrical signals being constrained to be in a direction aligned with said first axis and at most one of said second and third axes.

7. The apparatus of claim 1, wherein said geometric structure has a first radius of curvature and a second radius of curvature, and wherein a ratio of said second radius of curvature to said first radius of curvature is selected to attain a predetermined focus steering range and a spatial averaged intensity at a focus of the transducer.

8. The apparatus of claim 1, wherein said geometric structure has a first radius of curvature and a second radius of curvature, and wherein a ratio of said second radius of curvature to said first radius of curvature is between 60% and 70%.

9. The apparatus of claim 1, wherein said electrodes are configured to receive electrical signals that have been selected to generate first and second focal zones, said first focal zone being steerable independently of said second focal zone.

10. The apparatus of claim 9, wherein said electrodes are configured to receive electrical signals that have been selected to simultaneously steer said first and second focal zones to cause said first and second zones to merge into a third focal zone, said third focal zone being movable within a focusing range.

11. A method for designing a dual-curvature transducer array for use with a high intensity focused ultrasound medical system, said method comprising: determining a number of transducer elements for a surface of said dual-curvature transducer array based at least in part on a focus steering ability; applying an independent driving ultrasonic method or a symmetric ultrasonic driving method to said transducer elements; determining an aperture width of said surface of said dual-curvature transducer array based at least in part on total acoustic power of said dual-curvature transducer array; and determining a ratio of radii of dual curvatures to form a geometric shape of said dual-curvature transducer based at least in part on an intensity of acoustic energy absorption and a focus-steering range in a desired heating area, wherein said geometric shape is a truncated torus.

12. A method for using a high intensity focused ultrasound medical system having a dual-curvature transducer array having a plurality of transducer elements that are made from piezocomposite material, said transducer elements bonded together with an adhesive and deployed along a geometric structure with two curvatures, and electrodes arranged on said dual-curvature transducer array for exciting said transducer elements to emit ultrasonic waves in response to electrical signals applied to said electrodes to form or to be steered to a common focus zone in a desired heating area, said method comprising positioning said transducer on said desired heating area, determining a position of a focus zone in said desired heating area, and applying electric signals to excite said transducer elements, each of said signals having a frequency, phase, and amplitude selected to excite said transducer elements to cause steering of said ultrasonic waves to said focus zone, wherein said geometric structure is a truncated torus.

13. The method of claim 12, further comprising using a magnetic resonance imaging system to determine a position of said desired heating area and said focus zone.

* * * * *